US012005002B2

(12) United States Patent
Fu et al.

(10) Patent No.: US 12,005,002 B2
(45) Date of Patent: Jun. 11, 2024

(54) RE-TREATABLE CORNEAL LENTICULAR INCISIONS WITH RE-TREATMENT OPTIONS USING A FEMTOSECOND OPHTHALMIC LASER SYSTEM

(71) Applicant: AMO Development, LLC, Irvine, CA (US)

(72) Inventors: Hong Fu, Pleasanton, CA (US); Alireza Malek Tabrizi, Fremont, CA (US)

(73) Assignee: AMO Development, LLC, Irvine, CA (US)

( * ) Notice: Subject to any disclaimer, the term of this patent is extended or adjusted under 35 U.S.C. 154(b) by 282 days.

(21) Appl. No.: 17/449,249

(22) Filed: Sep. 28, 2021

(65) Prior Publication Data

US 2022/0096274 A1 Mar. 31, 2022

Related U.S. Application Data

(60) Provisional application No. 63/085,985, filed on Sep. 30, 2020.

(51) Int. Cl.
*A61F 9/008* (2006.01)
(52) U.S. Cl.
CPC ............ *A61F 9/00829* (2013.01); *A61F 2009/00872* (2013.01)
(58) Field of Classification Search
CPC ........... A61F 9/00829; A61F 9/00827; A61F 2009/00872; A61F 2009/00878; A61F 2009/00897; A61F 9/009
See application file for complete search history.

(56) References Cited

U.S. PATENT DOCUMENTS 5,439,462 A * 8/1995 Bille ................ A61F 9/00812
606/4
7,887,532 B2 * 2/2011 Kurtz ................ A61F 9/00831
606/166

(Continued)

FOREIGN PATENT DOCUMENTS

DE 102007019814 A1 10/2008
DE 102008056488 A1 5/2010

(Continued)

*Primary Examiner* — Carl H Layno
*Assistant Examiner* — Manolis Pahakis
(74) *Attorney, Agent, or Firm* — Johnson & Johnson Surgical Vision, Inc.

(57) ABSTRACT

A corneal lenticule extraction procedure provides convenient re-treatment options when treatment interruptions occur. The procedure is executed by an ophthalmic laser system according to a programmed treatment plan, which defines an entry cut, an optional ring cut, a bottom lenticule incision having an optical zone, and a flat top bed incision. If an interruption occurs during the entry cut, the treatment plan is re-aligned with the partially formed entry cut and continued, or with a new entry cut placed at a different angular position. If an interruption occurs during the ring cut, the treatment plan is revised to define a larger ring cut concentric with the partially formed ring cut. If an interruption occurs during the bottom or top incision, the depth of the partially formed bottom or top incision is measured, and the treatment plan is revised to form a deeper bottom incision or a shallower top incision, respectively.

21 Claims, 8 Drawing Sheets

(56) References Cited

U.S. PATENT DOCUMENTS

| | | | |
|---|---|---|---|
| 8,182,471 B2 | 5/2012 | Yee | |
| 9,855,170 B2 | 1/2018 | Bischoff et al. | |
| 9,962,292 B2* | 5/2018 | Bergt | A61F 9/00827 |
| 10,369,052 B2 | 8/2019 | Fu | |
| 10,653,557 B2* | 5/2020 | Rill | A61F 9/00825 |
| 10,779,988 B2 | 9/2020 | Fu et al. | |
| 11,000,413 B2* | 5/2021 | Simoneau | A61B 3/102 |
| 11,406,536 B2* | 8/2022 | Schuele | A61F 9/00804 |
| 2009/0171327 A1* | 7/2009 | Kurtz | A61F 9/009 |
| | | | 606/6 |
| 2009/0171329 A1* | 7/2009 | Raksi | A61F 9/00814 |
| | | | 606/5 |
| 2009/0312749 A1* | 12/2009 | Pini | A61F 9/0008 |
| | | | 606/4 |
| 2010/0305553 A1* | 12/2010 | Kittelmann | A61F 9/00836 |
| | | | 606/4 |
| 2012/0296321 A1* | 11/2012 | Frey | A61F 9/00827 |
| | | | 606/166 |
| 2013/0211390 A1* | 8/2013 | Bor | A61F 9/00829 |
| | | | 606/5 |
| 2014/0155875 A1* | 6/2014 | Bergt | A61F 9/00827 |
| | | | 606/5 |
| 2018/0000647 A1* | 1/2018 | Malek Tabrizi | A61B 3/0008 |
| 2018/0110654 A1* | 4/2018 | Rill | A61F 9/00838 |
| 2020/0064622 A1 | 2/2020 | Rahaman et al. | |
| 2020/0069470 A1 | 3/2020 | Fu et al. | |
| 2020/0222239 A1* | 7/2020 | Bischoff | A61F 9/00836 |
| 2021/0186759 A1* | 6/2021 | Sedky | A61F 9/00827 |
| 2021/0330501 A1* | 10/2021 | Bischoff | A61F 9/00825 |
| 2021/0401622 A1* | 12/2021 | Rathjen | A61F 9/008 |
| 2022/0280338 A1* | 9/2022 | Böhme | A61F 9/00825 |

FOREIGN PATENT DOCUMENTS

| | | |
|---|---|---|
| DE | 102017207529 A1 | 11/2018 |
| WO | 2018005877 A1 | 1/2018 |
| WO | 2020039328 A1 | 2/2020 |

* cited by examiner

RE-TREATABLE CORNEAL LENTICULAR INCISIONS WITH RE-TREATMENT OPTIONS USING A FEMTOSECOND OPHTHALMIC LASER SYSTEM

CROSS REFERENCE TO RELATED APPLICATIONS

This application claims the benefit under 35 U.S.C. § 119(e) of U.S. Provisional Patent Application No. 63/085,985, filed Sep. 30, 2020, which is incorporated herein by reference in its entirety.

BACKGROUND OF THE INVENTION

Field of the Invention

This invention relates generally to laser-assisted ophthalmic procedures, and more particularly, to a systems and methods for corneal lenticule extraction procedures with re-treatable corneal lenticule incisions.

Description of Related Art

Vision impairments such as myopia, hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and corneal lenticule extraction.

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In the corneal lenticule extraction procedure, instead of ablating corneal tissue with an excimer laser following the creation of a corneal flap, the technique involves tissue removal with two femtosecond laser incisions that intersect to create a lenticule for extraction. The extraction of the lenticule changes the shape of the cornea and its optical power to accomplish vision correction. Lenticule extractions can be performed either with or without the creation of a corneal flap. With the flapless procedure, a refractive lenticule is created in the intact portion of the anterior cornea and removed through a small incision.

In a conventional corneal lenticule extraction procedure, the lenticule incision process includes the following three segments in the order they are executed: First, forming the bottom lenticule incision, which includes a bottom optical zone and a bottom transition zone; second, forming a top lenticule incision, which includes a top optical zone and a top transition zone; and third, forming an entry cut. The top and bottom optical zones are located at the center of the respective lenticule incisions and have surface shapes that are determined by the optical power correction to be achieved by the lenticule extraction procedure, while the top and bottom transition zones are located outside of the respective optical zones and have shapes that are not determined by the optical power correction to be achieved but are influenced by other considerations such as mechanical properties of the formed lenticule which affect the ease of extraction, etc. The bottom and top lenticule surfaces typically have the same diameter (e.g., 6-8 mm). The top and bottom incisions intersect each other (and extend beyond the intersection line) to isolate a lenticule volume. The entry cut is formed near the periphery of the lenticule to provide an entry port for extracting the lenticule from the cornea.

During the lenticule incision process, treatment interruptions may occasionally occur, due to various system and process failures such as suction loss in the patient interface device (a device that mechanically couples the patient's eye to the ophthalmic laser system). Such interruptions prevent the completion of the full lenticule formation and may oblige the surgeon to switch to a PRK or LASIK procedure as a re-treatment option. As PRK and LASIK involves a different laser system than corneal lenticule extraction (excimer laser vs. femtosecond laser), this re-treatment option is inconvenient for the patient.

SUMMARY

Accordingly, the present invention is directed to a method and related apparatus of forming a corneal lenticule that substantially obviates one or more of the problems due to limitations and disadvantages of the related art.

An object of the present invention is to provide a re-treatable corneal lenticule formation process and to provide retreatment options that can be performed with the same femtosecond laser system.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a corneal lenticule formation method implemented in an ophthalmic laser system for forming a lenticule in a cornea of a patient's eye, which includes: (a) generating a laser beam; (b) scanning a laser beam focal spot in the cornea by executing a treatment plan, the treatment plan including a bottom segment defining a bottom lenticule incision and a top segment defining a top bed incision, wherein the bottom lenticule incision includes an optical zone having a shape determined by a defined optical power of the lenticule, the top bed incision has a flat shape, and the top bed incision is located above the bottom lenticule incision and has a smaller diameter than a diameter of the bottom lenticule incision; (c) in response to an interruption while executing the bottom segment of the treatment plan after a bottom lenticule incision is partially formed, revising the treatment plan to define a new bottom lenticule incision which is located below the partially formed bottom lenticule incision, and scanning the laser beam focal spot by executing the revised treatment plan to form the new bottom lenticule incision; and (d) in response to an interruption while executing the top segment of the treatment plan after a top bed incision is partially formed, revising the treatment plan to define a new top bed incision which is located above the partially formed top bed incision, and scanning the laser beam focal spot by executing the revised treatment plan to form the new top bed incision.

In another aspect, the present invention provides a corneal lenticule formation method implemented in an ophthalmic laser system for forming a lenticule in a cornea of a patient's eye, which includes: (a) generating a laser beam; (b) scanning a laser beam focal spot in the cornea by executing a treatment plan, the treatment plan including, in a sequence, an entry segment defining an entry cut, a bottom segment defining a bottom lenticule incision, and a top segment defining a top bed incision, wherein the bottom lenticule incision includes an optical zone having a shape determined by a defined optical power of the lenticule, the top bed incision has a flat shape, the top bed incision is located above the bottom lenticule incision and has a smaller diameter than a diameter of the bottom lenticule incision, the top bed incision and the bottom lenticule incision intersect each other near their respective peripheries to define an isolated lenticule volume, and the entry cut has a band shape and extends upwardly from an outer edge of the bottom lenticule incision; (c) in response to an interruption while executing the entry segment of the treatment plan after am entry cut is partially formed, revising the treatment plan to define a new entry cut that is aligned with the partially formed entry cut, a new bottom lenticule incision, and a new top bed incision, and scanning the laser bean by executing the revised treatment plan to complete the entry cut and to form the new bottom lenticule incision and the new top bed incision; (d) in response to an interruption while executing the bottom segment of the treatment plan after an entry cut is formed and a bottom lenticule incision is partially formed, revising the treatment plan to define a new bottom lenticule incision which is located below the partially formed bottom lenticule incision and a new top bed incision located above new bottom lenticule incision, and scanning the laser beam focal spot by executing the revised treatment plan to form the new bottom lenticule incision and the new top bed incision; and (e) in response to an interruption while executing the top segment of the treatment plan after an entry cut and a bottom lenticule incision are formed and a top bed incision is partially formed, revising the treatment plan to define a new top bed incision which is located above the partially formed top bed incision, and scanning the laser beam focal spot by executing the revised treatment plan to form the new top bed incision.

In another aspect, the present invention provides a corneal lenticule formation method implemented in an ophthalmic laser system for forming a lenticule in a cornea of a patient's eye, which includes: (a) generating a laser beam; (b) scanning a laser beam focal spot in the cornea by executing a treatment plan, the treatment plan including, in a sequence, an entry segment defining an entry cut, a ring segment defining a ring cut, a bottom segment defining a bottom lenticule incision, and a top segment defining a top bed incision, wherein the bottom lenticule incision includes an optical zone having a shape determined by a defined optical power of the lenticule, the top bed incision has a flat shape, the top bed incision is located above the bottom lenticule incision and has a smaller diameter than a diameter of the bottom lenticule incision, the ring cut has a ring shape and extends between the top bed incision and the bottom lenticule incision, both the top bed incision and the bottom lenticule incision intersect the ring cut near their respective peripheries to define an isolated lenticule volume, and the entry cut has a band shape and extends upwardly from an outer edge of the bottom lenticule incision; (c) in response to an interruption while executing the entry segment of the treatment plan after an entry cut is partially formed, revising the treatment plan to define a new entry cut that is aligned with the partially formed entry cut, a new ring cut, a new bottom lenticule incision, and a new top bed incision, and scanning the laser bean by executing the revised treatment plan to complete the entry cut and to form the new ring cut, the new bottom lenticule incision and the new top bed incision; (d) in response to an interruption while executing the ring segment of the treatment plan after an entry cut is formed and a ring cut is partially formed, revising the treatment plan to define a new ring cut that has a radius larger than a radius of the partially formed ring cut and is aligned concentrically with the partially formed ring cut, a new bottom lenticule incision, and a new top bed incision, and scanning the laser bean by executing the revised treatment plan to form the new ring, the new bottom lenticule incision and the new top bed incision; (e) in response to an interruption while executing the bottom segment of the treatment plan after an entry cut and a ring cut are formed and a bottom lenticule incision is partially formed, revising the treatment plan to define a new bottom lenticule incision which is located below the partially formed bottom lenticule incision and a new top bed incision located above the new bottom lenticule incision, and scanning the laser beam focal spot by executing the revised treatment plan to form the new bottom lenticule incision and the new top bed incision; and (f) in response to an interruption while executing the top segment of the treatment plan after an entry cut, a ring cut and a bottom lenticule incision are formed and a top bed incision is partially formed, revising the treatment plan to define a new top bed incision which is located above the partially formed top bed incision, and scanning the laser beam focal spot by executing the revised treatment plan to form the new top bed incision.

In some embodiments, the radius of the new ring cut is larger than the radius of the partially formed ring cut by 20-100 microns, the apex of the new bottom lenticule incision is located 5-20 microns below the apex of the partially formed bottom lenticule incision, and the new top bed incision is located 5-10 microns above the partially formed top bed incision.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provide improved corneal lenticule incision formation methods implemented in a femtosecond ophthalmic laser system, which provide re-treatment options after an interruption during the procedure. The re-treatment options are accomplished using the same femtosecond laser system without the need to change to a PRK or LASIK procedure.

Figure 1:
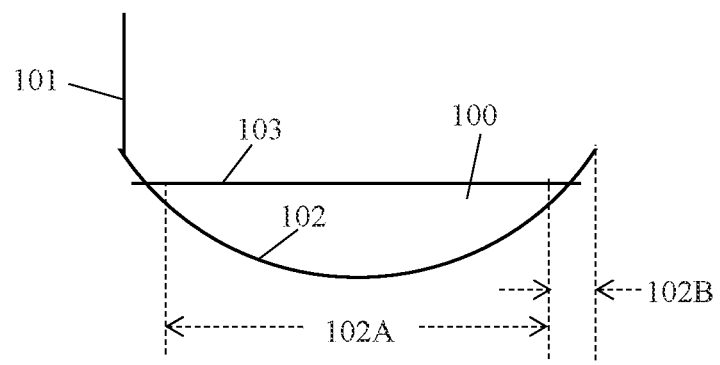
FIG. 1 schematically illustrates a corneal lenticule formed according to a first embodiment of the present invention.

In a corneal lenticule extraction procedure according to a first embodiment of the present invention, the lenticule incision process includes the following three segments in the order they are executed (see FIG. 1, side view): an entry cut 101, a bottom lenticule incision 102, and a flat top bed incision 103. Note that "incision" and "cut" are used interchangeably in this disclosure. The bottom lenticule incision preferably has a larger diameter (e.g., 8 mm) than that of the top bed incision (e.g., 6 mm), and the top and bottom incisions intersect each other near their peripheries to form an isolated lenticule volume 100 to be extracted. The entry cut is a band shaped incision located along the outer edge of the bottom lenticule incision, extending upwardly, and optionally outwardly, to reach the anterior corneal surface to provide an entry port for extracting the lenticule from the cornea.

The bottom lenticule incision 102 includes a bottom optical zone 102A located in the center area, and optionally a bottom transition zone 102B surrounding the bottom optical zone. The shape of the bottom optical zone 102A is determined by the optical power correction to be achieved by the lenticule extraction procedure. As the top bed incision is flat, the optical zone of the bottom incision provides all of the optical power of the lenticule. The transition zone 102B has a shape that is not determined by the optical power correction to be achieved but is influenced by other considerations such as mechanical properties of the formed lenticule which affect the ease of extraction.

Figure 2:
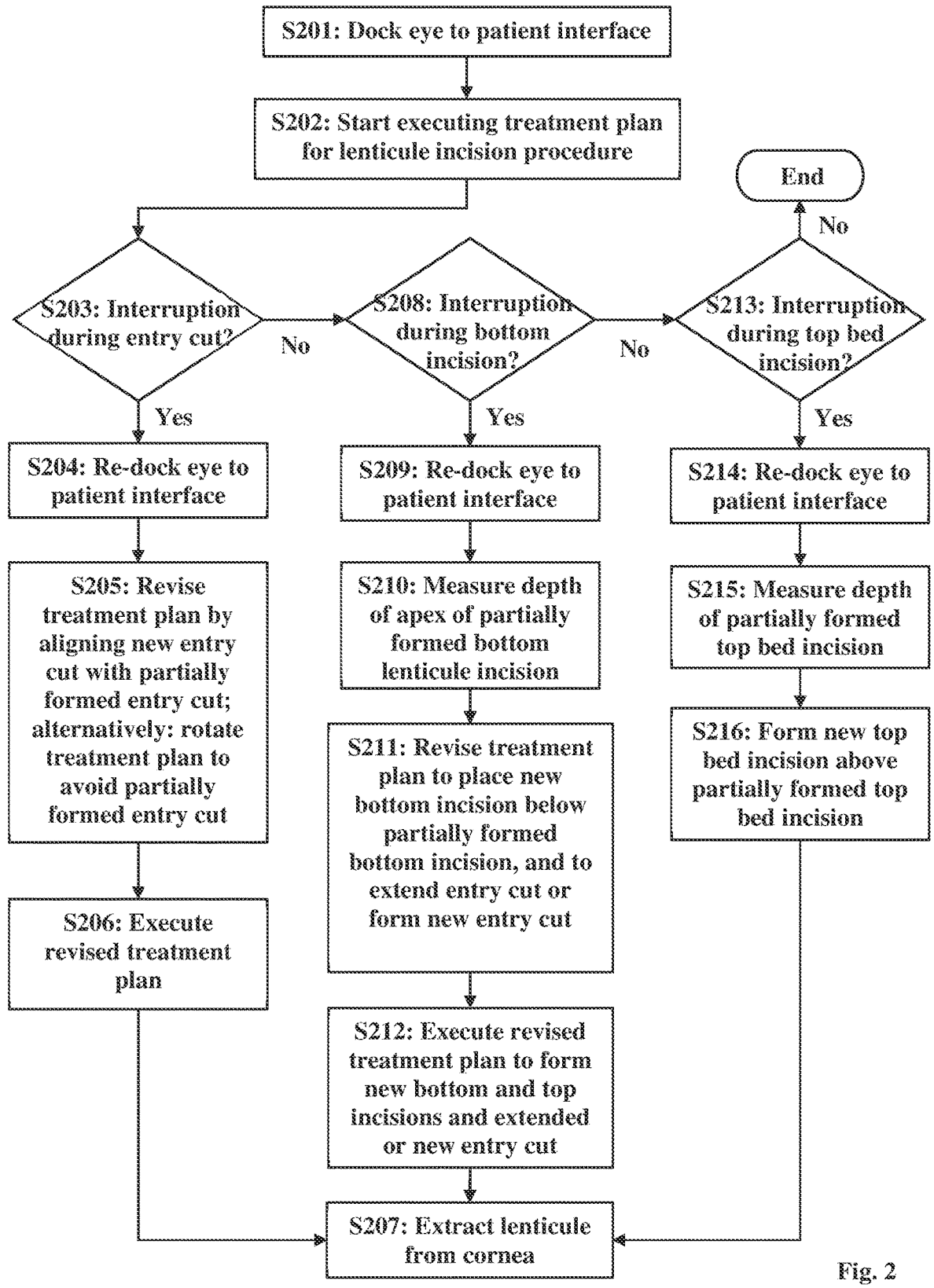
FIG. 2 schematically illustrates a process of forming a corneal lenticule with re-treatment options according to the first embodiment.

During the lenticule incision process, if the treatment is interrupted, for example, due to suction loss in the patient interface device, different sets of re-treatment steps are performed depending on the stage at which the treatment is interrupted. A corneal lenticule exaction procedure with re-treatment options according to the first embodiment of the present invention is described with reference to FIG. 2.

After the patient's eye is coupled to the laser system via a patient interface device (commonly referred to as docking) (step S201), the planned lenticule incision procedure starts (step S202). As described earlier, the planned lenticule incision procedure includes forming an entry cut, then forming a bottom lenticule incision, and then forming a flat top bed incision. The parameters of the incisions are used to program a treatment plan, which includes various segments that define the various incisions. The lenticule incision procedure is carried out by the ophthalmic laser system under the control of a system controller (e.g. a computer) which executes the treatment plan. If a failure event occurs, the computer automatically interrupted the execution of the treatment plan. The surgeon then takes the necessary actions and instructs the computer to perform re-treating steps as described below.

If the procedure is interrupted while forming the entry cut (i.e., an interruption occurs while executing the entry cut segment of the treatment plan) ("Yes" in step S203), the surgeon re-docks the eye to the laser system via the patient interface if necessary (step S204). Then, the original treatment plan is revised by aligning its entry cut with the partially formed entry cut (step S205), and the planned lenticule incision procedure is continued with the revised (aligned) treatment plan to form the uncompleted part of the entry cut (i.e. skipping the already formed part of the entry cut), the top bed incision and the bottom lenticule incision (step S206). After the re-treatment is successfully completed, the lenticule is extracted from the cornea (step S207).

The alignment step (step S205) may be performed by the surgeon with the assistance of a user interface display of the ophthalmic laser system. The user interface display displays an image of the patient's eye where the partially formed entry cut is visible, and overlays a representation of the incisions (at least the entry cut) drawn according to the treatment plan. Using the user interface display, the surgeon may move the representation of the incisions to align with the partially formed entry cut in the eye image, and the computer revises the treatment plan accordingly. The alignment step is required because of potential shift and rotation of the re-docket eye relative to its position before the interruption. Except for any shift and rotation, the revised treatment plan is otherwise the same as the original treatment plan. Step S206 is performed in response to the surgeon's instruction.

Because the entry cut is only used for a lenticule removal tool to access and extract the lenticule, the shape of the entry cut does not affect the optical power of the lenticule. Therefore, the alignment precision of the partially formed entry cut with the continued entry cut has a relatively low precision requirement.

In an alternative embodiment, in step S205, the partially formed entry cut is disregarded, and the original treatment plan is revised by moving the entry cut position to a new angular position that avoids the partially formed entry cut, and the revised treatment plan is executed to form a new entry cut, a bottom lenticule incision and a top bed incision.

If the procedure is interrupted while forming the bottom lenticule incision ("Yes" in step S208), the surgeon re-docks the eye to the laser system via the patient interface if necessary (step S209), and the depth of the apex (the lowest point) of the partially formed bottom lenticule incision is measured using a depth measurement subsystem of the ophthalmic laser system (step S210). Then, the treatment plan is revised, by shifting the bottom and top incisions downwardly so that the apex of the new bottom lenticule incision is located at a predetermined distance below the apex of the partially formed bottom lenticule incision as measured in step S210 (step S211). The predetermined distance may be, for example, 5-20 microns, or more preferably, about 10 microns. The new bottom lenticule incision and the top bed incision otherwise have the same parameters as in the original treatment plan, including the distance between the bottom and top incisions. The new bottom lenticule incision is not required to be precisely aligned vertically with the partially formed bottom lenticule incision. The revised treatment plan may also include an extension of the already formed entry cut downwardly to reach the now deeper bottom lenticule incision (this will require aligning the revised treatment plan to the already formed entry cut using the earlier described technique), or alternatively, include a new entry cut at a different angular location. The revised treatment plan is executed to form a new bottom lenticule incision and a top bed incision (step S212). After the re-treatment is successfully completed, the lenticule is extracted from the cornea (step S207). Steps S210-S212 are performed in response to the surgeon's instruction.

Figure 1A:
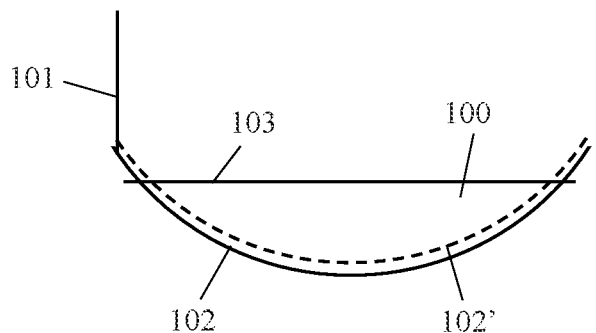
FIGS. 1A and 1B schematically illustrate corneal lenticules formed by re-treatment steps according to the first embodiment.

FIG. 1A schematically illustrates the partially formed bottom lenticule incision 102', the new bottom lenticule incision 102, the top bed incision 103, and the entry cut 101 (new or extended). The lenticule volume 100 is isolated by the new bottom lenticule incision 102 and the top bed incision 103. Because the original bottom lenticule incision 102' is incomplete, e.g. it does not extend the entire 360 degrees angular range in the top view, it will not form an isolated volume with the top bed incision 103 or with the new bottom lenticule incision 102. Thus, the lenticule volume can be removed with minimal complications.

In preferred embodiments, the bottom lenticule incision is formed by placing a short laser scan line in a direction tangential to the parallels of latitude of the bottom lenticule incision and scanning it along meridians of longitude of the bottom lenticule surface to form multiple sweeps (described in more detail later). Since each sweep passes the apex of the lenticule, the apex is formed after the first scan. Thus, in the majority of the cases, the apex is at least partially formed when the interruption occurs during bottom surface formation, so its depth can be measured in step S210.

The depth of the apex may be measured using a non-confocal detector of the ophthalmic laser system, which detects a reflected laser beam that is reflected by the partially formed bottom incision and collected by the objective lens of the laser system. Details of such a depth measurement subsystem is described in commonly owned U.S. Pat. Appl. Pub. No. 2020/0064622, entitled "Detection of Optical Surface of Patient Interface for Ophthalmic Laser Applications Using a Non-Confocal Configuration," the disclosure of which is incorporated herein by reference. The depth of the apex may also be measured using an optical coherence tomography (OCT) subsystem of the ophthalmic laser system.

In this re-treatment option, when forming the new bottom lenticule incision at a deeper depth, care should be taken to avoid the adverse impact of gas bubbles. Gas bubbles are often created at the incision site when incising corneal tissue using a femtosecond pulsed laser. Such gas bubbles may interfere with the formation of a subsequent incision at a deeper depth. Thus, if gas bubbles generated when incising the originally planned bottom lenticule incision 102' are still remaining, they may be eliminated through the entry cut, or the new bottom lenticule incision may be formed after a sufficient time has passed to allow the gas bubbles to disappear.

If the procedure is interrupted while forming the top bed incision ("Yes" in step S213), the surgeon re-docks the eye to the laser system via the patient interface if necessary (step S214), and the depth of the partially formed top bed incision is measured using the depth measurement subsystem of the ophthalmic laser system (step S215). Then, a revised treatment plan is generated and executed to form a new top bed incision at a depth that is shallower than the partially formed top bed incision by a predetermined distance (step S216). The predetermined distance may be, for example, 5-10 microns. Because the bottom lenticule incision is larger than the originally planned top bed incision by a sufficient amount, the new shallower top bed incision will still intersect the bottom lenticule incision around the entire periphery to form an isolated lenticule volume. After the re-treatment is successfully completed, the lenticule is extracted from the cornea (step S207). Steps S215-S216 are performed in response to the surgeon's instruction.

Figure 1B:
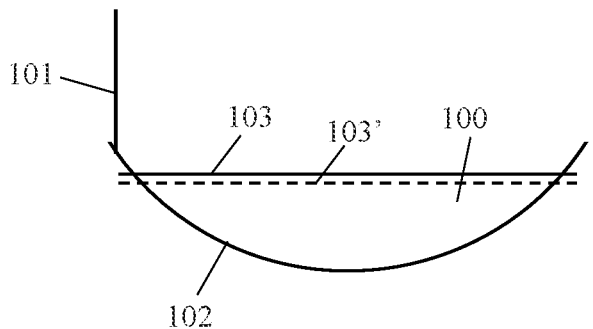

FIG. 1B schematically illustrates the entry cut 101, the bottom lenticule incision 102, the partially formed top bed incision 103', and the new top bed incision 103. The new top bed incision 103 and the bottom lenticule incision 102 form the isolated lenticule volume 100. Because the original top bed incision 103' is incomplete, it will not form an isolated volume with the top bed incision 103 or with the bottom lenticule incision 102. Thus, the lenticule volume can be removed with minimal complications.

Because the top bed incision is flat, there is no need to vertically align the top bed incision with the already formed bottom lenticule incision. Had the top incision been a lenticule shape, the apex of the top lenticule would have to be precisely aligned with the apex of the bottom lenticule incision.

In an alternative embodiment, in the original treatment plan, the entry cut is formed after the bottom lenticule incision and the top bed incision. If the procedure is interrupted while forming the entry cut, a revised plan for the entry cut is aligned with the partially formed entry cut similar to step S205, and the entry cut is continued using the revise plan. The re-treatment steps for interrupted bottom and top incisions remain the same as described above.

In another alternative embodiment, in the original treatment plan, the top bed incision is formed before the bottom lenticule incision. If the procedure is interrupted while forming the top bed incision, the depth of the partially formed top bed incision is measured, and a new top bed incision and a bottom lenticule incision are formed by executing a revised treatment plan, where the top and bottom incisions are shifted upwardly so that the new top bed incision is located at a predetermined distance above the partially formed top bed lenticule incision. The result is similar to that shown in FIG. 1B. In this alternative embodiment, if the procedure is interrupted while forming the bottom lenticule incision, the depth of the apex of the partially formed bottom lenticule incision is measured, and a new bottom lenticule incision is formed by executing a revised treatment plan, where the new bottom lenticule incision is located at a predetermined distance deeper than the partially formed bottom lenticule incision. The result is similar to that shown in FIG. 1A.

In another alternative embodiment, the entry cut is merged with the bottom incision into one segment; i.e., when forming the bottom incision, some of the scanning of the laser scan line are extended upwards to reach the anterior corneal surface to form the entry cut. In this embodiment, if the procedure is interrupted while forming the bottom lenticule incision, the treatment plan is revised to place the bottom lenticule incision below the partially formed bottom lenticule incision as described earlier, and also to rotate the location of the entry port, to form a new bottom lenticule incision with entry cut.

Figure 3:
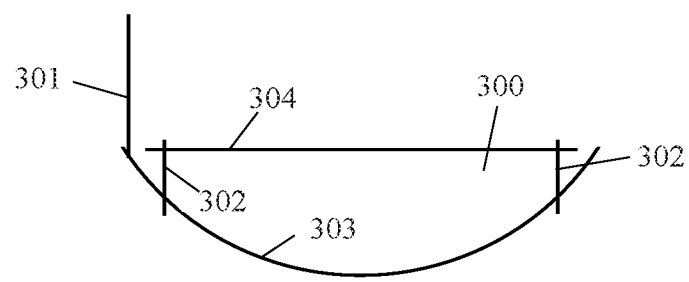
FIG. 3 schematically illustrates a corneal lenticule formed according to a second embodiment of the present invention.
Figure 3A:
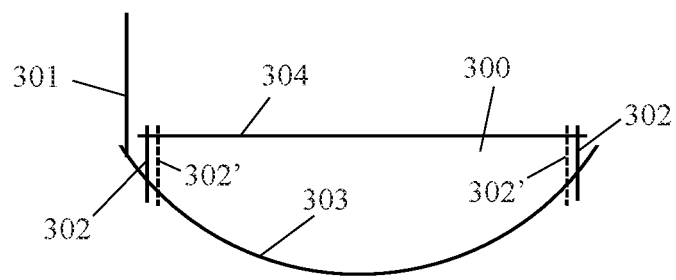
FIG. 3A schematically illustrates a corneal lenticules formed by re-treatment steps according to the second embodiment.
Figure 4:
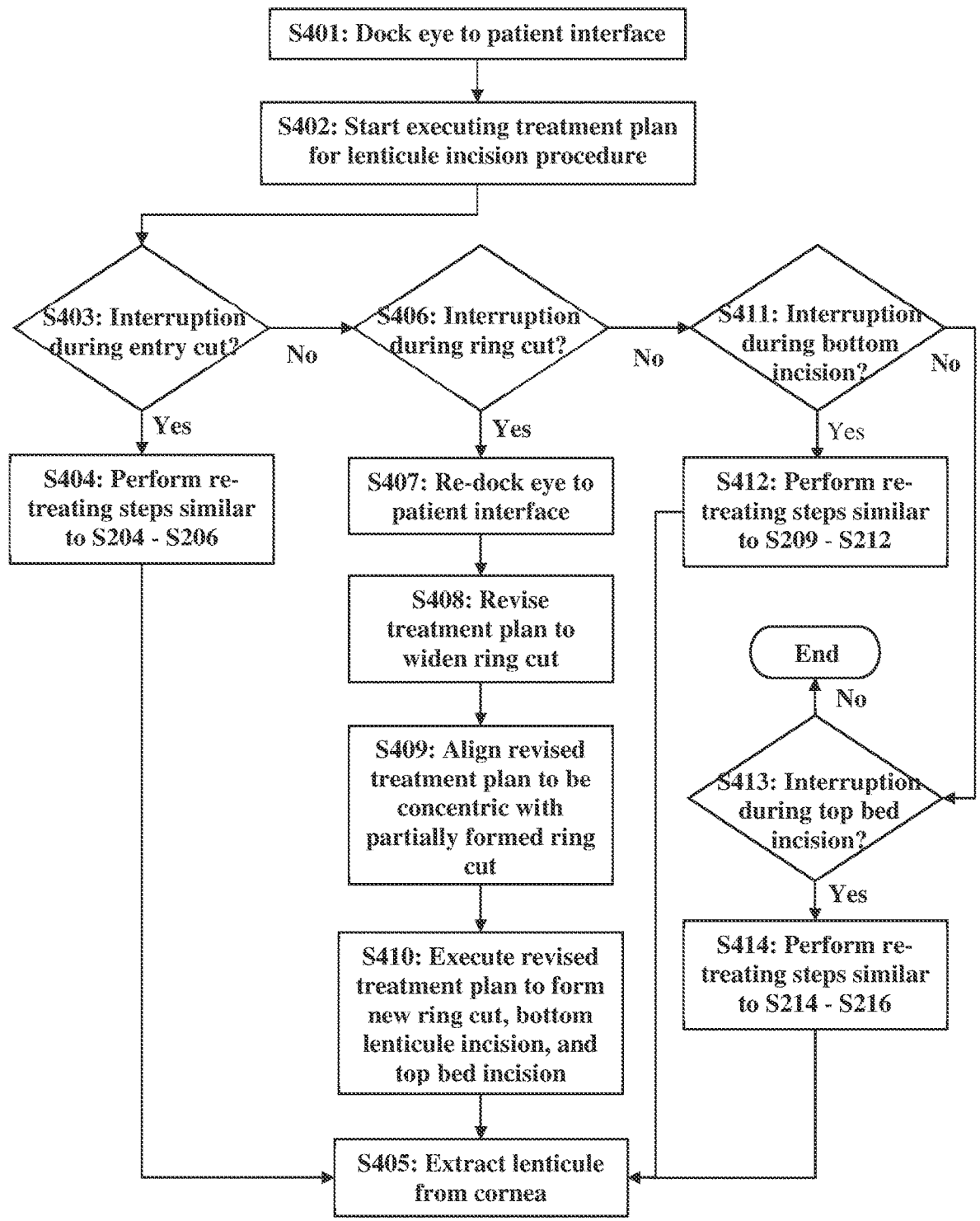
FIG. 4 schematically illustrates a process of forming a corneal lenticule with re-treatment options according to the second embodiment.

FIGS. 3, 3A and 4 schematically illustrate a corneal lenticule extraction procedure according to a second embodiment of the present invention. The corneal lenticule incisions in this embodiment include the following four segments in the order they are executed (see FIG. 3, side view): an entry cut 301, a ring cut 302, a bottom lenticule incision 303, and a flat top bed incision 304. The ring cut has a ring shape, extending between the top and bottom incisions in a substantially vertical direction either with or without an inclination angle. The top and bottom incisions do not intersect each other, but both intersect the ring cut near their peripheries to form an isolated lenticule volume 300 to be extracted. The entry cut is a band shaped incision located along the outer edge of the bottom lenticule incision, the outer edge of the top bed incision, or the ring cut. The lenticule formed with the ring cut has a thicker edge than the lenticule in the first embodiment of FIG. 1, making it easier to extract. Other aspects of the corneal lenticule incisions are similar to those of the first embodiment of FIG. 1.

In the second embodiment, as shown in FIG. 4, after the patient's eye is docked to the laser system via a patient interface device (step S401), the planned lenticule incision procedure starts (step S402).

If the procedure is interrupted while forming the entry cut ("Yes" in step S403), re-treating steps similar to those in the first embodiment (steps S204 to S206) are performed (steps S404). After the re-treatment is successfully completed, the lenticule is extracted from the cornea (step S405).

If the procedure is interrupted while forming the ring cut ("Yes" in step S406), the surgeon re-docks the eye to the laser system via the patient interface if necessary (step S407), and the original treatment plan is revised to define a ring cut with a slightly larger radius (e.g., by 20-100 microns) than the original ring cut (step S408). The revised treatment plan may include a new entry cut as well, but the parameters of the bottom lenticule incision and top bed incision are preferably unchanged. The revised treatment plan is aligned with the partially formed ring cut so that the new ring cut is concentric with the partially formed ring cut (step S409). The alignment may be done with the assistance of the user interface display of the ophthalmic laser system, similar to step S205. The revised treatment plan is executed to form the new ring cut, the bottom lenticule incision and the top bed incision (step S410). After the re-treatment is successfully completed, the lenticule is extracted from the cornea (step S405). Steps S408-S410 are performed in response to the surgeon's instruction.

FIG. 3A schematically illustrates the partially formed ring cut 302', the new (wider) ring cut 302, the bottom lenticule incision 303, the top bed incision 304, and the entry cut 301. Because the original ring cut 302' is incomplete, it will not form an isolated volume with the top and bottom incisions 303 and 304 or with the new ring cut 302. Thus, the lenticule volume can be removed with minimal complications.

If the procedure is interrupted while forming the bottom lenticule incision ("Yes" in step S411), re-treating steps similar to those in the first embodiment (steps S209 to S212) are performed (steps S412). In other words, the bottom and top incisions are shifted downwardly relative to the partially formed bottom lenticule incision. If the procedure is interrupted while forming the top bed incision ("Yes" in step S413), re-treating steps similar to those in the first embodiment (steps S214 to S216) are performed (steps S414). In other words, the top bed incision is shifted upwardly relative to the partially formed top bed incision. After the re-treatment is successfully completed, the lenticule is extracted from the cornea (step S405).

In all of the embodiments described above, the new incisions (ring cut, bottom lenticule incision, top bed incision) of the revised treatment plan are located outside of the corresponding partially formed incisions. More specifically, the new bottom lenticule incision is located below the partially formed bottom lenticule incision, the new top bed incision is located below the partially formed top bed incision, and the new ring cut is located outside of the partially formed ring cut.

Figure 5A:
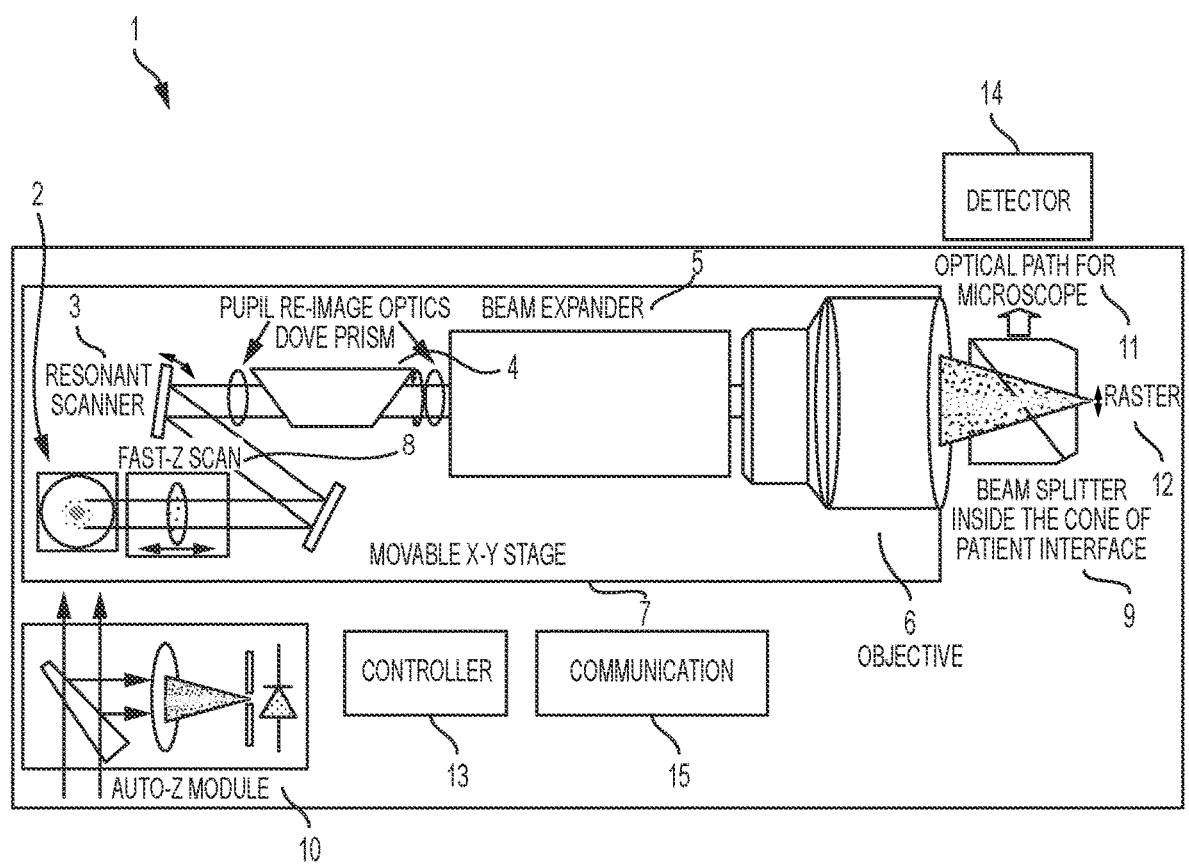
FIGS. 5A and 5B schematically illustrate two exemplary ophthalmic laser systems which may be used to implement embodiments of the present invention.
Figure 5B:
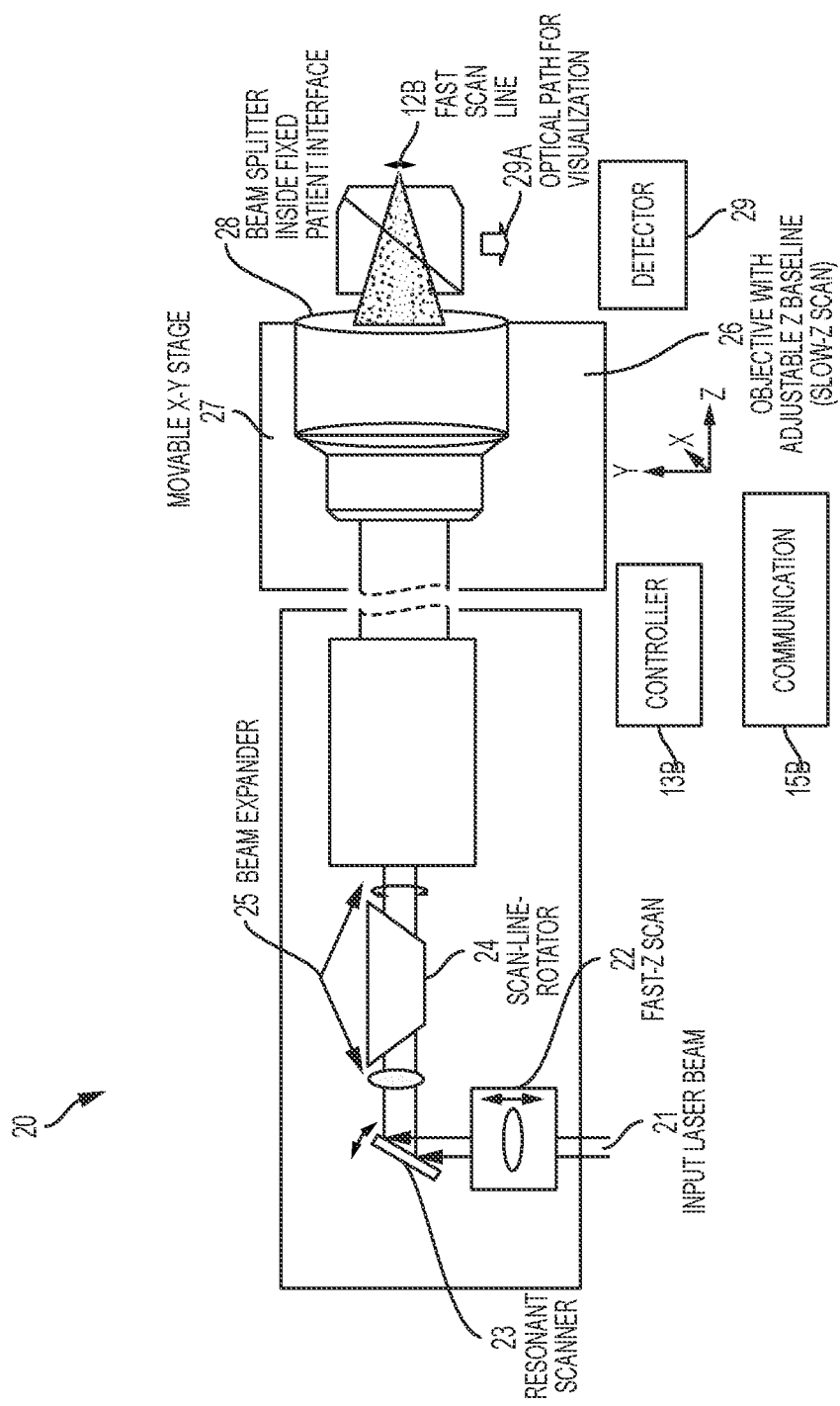

Ophthalmic laser systems that may be used to implement the above-described lenticule extraction procedures are described in more detail now with reference to FIGS. 5A and 5B.

FIG. 5A shows an ophthalmic surgical laser system 1 suitable for making an incision in a target material such as a cornea of an eye. A laser 2, such as a femtosecond laser, provides a pulsed laser beam 2A which may be used in optical procedures to treat the eye. The system 1 further includes, but is not limited to, a high frequency scanner (such as a resonant scanner) 3 for scanning the pulsed laser beam to produce a scan line 12 of the pulsed laser beam, a scan line rotator 4 for rotating the scan line 12, a beam expander 5, an objective 6 for focusing the laser beam, an XY scan device 7 for deflecting or directing the laser beam on or within the target, a fast-Z scan device 8, a patient interface 9, an auto-Z device 10, a controller 13, and a communication module 15.

The resonant scanner 3 scans the pulsed laser beam at a high resonant frequency (e.g., thousands of Hz) to produces the scan line that extends in a lateral orientation (i.e. a direction perpendicular to the laser beam propagation direction Z) and having a desired length, for example, between 1 mm and 2 mm. The length of the scan line may be adjustable. The scan line rotator 4 may be implemented by a Dove prism, a Pechan prism, a set of mirrors, or the like, mounted on a rotating stage. By rotating the scan line rotator 4 around the Z axis, the lateral orientation of the scan line 12 is rotated, so that the scan line may be placed at any desired orientation in the XY plane (i.e., the lateral plane perpendicular to the laser beam propagation direction Z). The XY scan device 7 may be a movable XY scanning stage having the focusing objective 6 mounted thereon; the XY scan device 7 carries the objective 6 and moves it relative to the patient interface device 9, so as to move the center of the scan line 12 relative to the patient's eye in the XY directions. The fast-Z scan device 8 changes the depth (i.e. along the Z direction) of the laser focal spot location in the eye. Thus, the scan line rotator 4 modifies the lateral orientation of the scan line 12 while the moveable XY scanning stage 7 and the fast-Z scan device 8 move the center of the scan line in X, Y and Z directions. Because the scanning speed of the resonant scanner is typically much faster than the speed of the XY scanning stage and the fast-Z scan device, the scan line 12 may be referred to as a fast scan line, and the movement of the fast scan line in X, Y and Z directions may be referred to as a slow sweep.

The XY scanning stage 7 may be a motorized stage with two motors that drive its movements in the X and Y directions. Preferably, the XY scanning stage is a recoilless stage configured to reduce or eliminate mechanical vibration. The fast-Z scan device 8 may include a voice coil actuator that drives a lens in the Z direction. Movements of the lens lead to a focus depth change. The fast-Z scan frequency may be between 50 Hz and 15,000 Hz.

The patient interface device 9 couples the patient's eye to the ophthalmic surgical laser system 1. The patient interface 9 may include a visualization beam splitter to reflect the light from the eye along an optical path 11 toward a video microscope or ocular microscope 14, to allow the eye to be imaged by an image detector of the microscope. The visualization beam splitter, optical path 11 and microscope 14 are optional.

The auto-Z module 10 may include either a confocal detector or a non-confocal detector, and may be used to measure depth of target surfaces as described in more detail in the above-mentioned U.S. Pat. Appl. Pub. No. 2020/0064622.

The controller 13, which may be implemented by a processor executing suitable machine-readable program code and data stored in a non-volatile memory, is operably coupled to the various components of the system 1 including the laser 2, the fast-Z scan device 8, the resonant scanner 3, the scan line rotator 4, the XY scanning stage 7, the detector 14, and the communication module 15. The controller 13 is configured to direct these components of the system to output the focal spot of the pulsed laser beam in a desired pattern in the eye so as to modify the eye. The communication module 15 provides information to the operator of the laser system 1 at the system and/or remotely via wired or wireless data connection, and may include displays, user input devices such as keyboard, mouse, joystick, etc. The ophthalmic surgical laser system may additionally include an OCT (optical coherence tomography) device (not shown in FIG. 5A) which may be used to measure structures of the target (e.g. eye tissues).

FIG. 5B shows an ophthalmic surgical laser system 20 suitable for making an incision in a target material such as a cornea of an eye. The system 20 includes, but is not limited to, a laser source (not shown) that generates an input pulsed laser beam 21, a fast-Z scan device 22, a resonant scanner 23 for producing a scan line 12B of the pulsed laser beam 21, a scan line rotator 24 for rotating the lateral orientation of the scan line 12B, a beam expander 25, an objective with an adjustable focusing mechanism (slow-Z scanner) 26, a XY scanning stage 27 for deflecting or directing the pulsed laser beam 21 on or within the target, a patient interface 28 that may optionally include a beam splitter, a controller 13B, an optional image detector 29 disposed on an optical path 29A defined by the beam splitter of the patient interface, and a communication module 15B. The slow-Z scanner 26 may be used to set the laser focal spot at a desired focal depth which may set the Z-baseline of the scan pattern.

One difference between the system of FIG. 5B and that of FIG. 5A is that the XY scanning stage 7 in FIG. 5A carries both the objective 6 and other components including the fast-Z scan device 8, resonant scanner 3, scan line rotator 4, and beam expander 5, while the XY scanning stage 27 in FIG. 5B carries the objective 26 but not the other components mentioned above. Note that the in the system of FIG. 5A, the objective 6 may also be equipped with a slow-Z scanner (also represented by reference symbol 6).

Further details of ophthalmic surgical laser systems having the configurations shown in FIGS. 5A and 5B are described in commonly owned U.S. patent application Ser. No. 14/970,898, filed Dec. 16, 2015, entitled "Compact Ultra-Short Pulsed Laser Eye Surgery Workstation," and Ser. No. 14/865,396, filed Sep. 25, 2015, entitled "Systems and Methods for Lenticular Laser Incision," which are incorporated herein by reference in their entireties.

Figure 6:
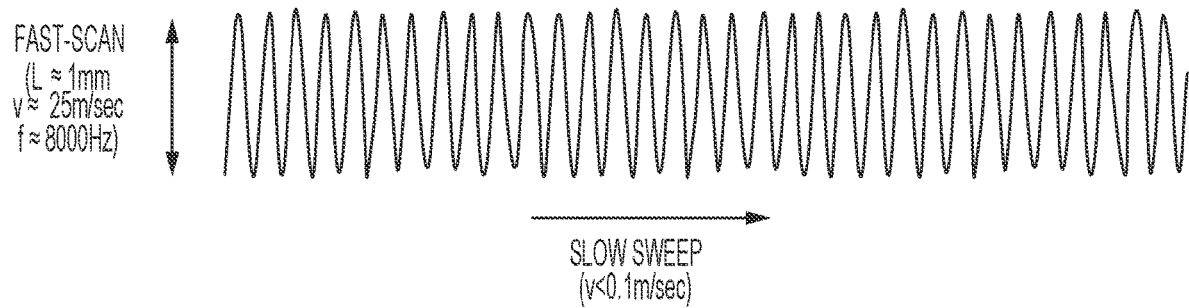
FIG. 6 illustrates an exemplary fast-scan-slow-sweep scheme in the ophthalmic laser systems of FIGS. 5A and 5B.

In the above ophthalmic laser systems, the beam scanning can be realized with a "fast-scan-slow-sweep" scanning scheme, also referred herein as a fast-scan line scheme. FIG. 6 illustrates a scanning example using an 8 kHz (e.g. between 7 kHz and 9 kHz) resonant scanner to produce a fast scan line 410 of about 1 mm (e.g., between 0.9 mm and 1.1 mm) and a scan speed of about 25 m/sec, and X, Y, and Z scan mechanisms with the scan speed (sweep speed) smaller than about 0.1 m/sec. The fast scan line 410 may be perpendicular to the optical beam propagation direction, i.e., it is always parallel to the XY plane. The trajectory of the slow sweep 420 can be any three dimensional curve drawn by the X, Y, and Z scanning devices (e.g., XY-scanner and fast-Z scanner). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 7:
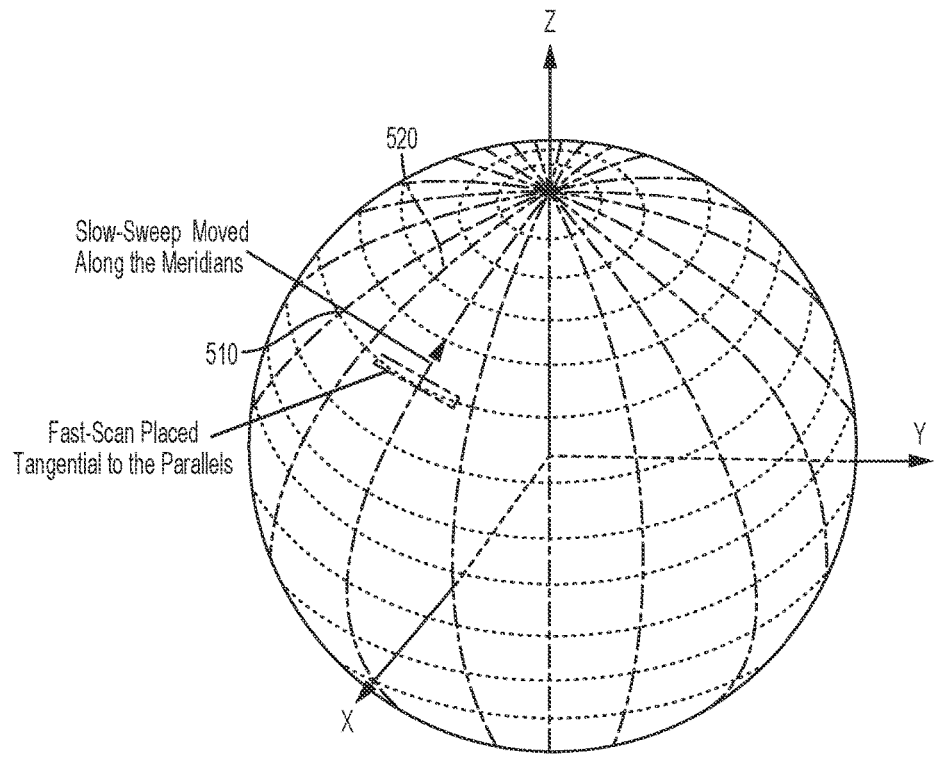
FIGS. 7 and 8 illustrate an exemplary lenticule surface incision method using a fast-scan-slow-sweep scheme of the ophthalmic laser systems of FIGS. 5A and 5B.

In an example shown in FIGS. 7 (perspective view) and 8 (top view), the laser system creates a smooth lenticular cut using the "fast-scan-slow-sweep" scanning scheme. First, in a three dimensional lenticular cut, the fast scan line is preferably placed tangential to the parallels of latitude 510 on the surface of the lenticule. A parallel of latitude is the intersection of the surface with a plane perpendicular to the Z axis (which is the axis parallel to the depth direction of the eye), i.e. a circle (or other closed lines) on the surface of the lenticule that is perpendicular to the Z axis and has a defined distance to the apex (intersection of the surface with the Z axis, also the highest or lowest point in the Z direction). For example, this can be realized by adjusting the scan line rotator to the corresponding orientations via software, e.g., via the controller. Second, the slow sweep trajectory preferably moves along the meridians of longitude 520 on the surface of the lenticule. A meridian of longitude is the intersection of the surface with a plane that passes through the Z axis, i.e. a curve that passes through the apex and has a defined angular direction with respect to the Z axis. For example, this can be done by coordinating the XY scanner and the Fast-Z scanner via the software, e.g., via the controller. The procedure starts with the scan line being parallel to the parallel of latitude, and sweeps through the apex of the lens, following the curvature with the largest diameter. Multiple sweeps are performed at successive angular directions with respect to the Z axis, for example as realized by rotating the scan line rotator between successive sweeps, to form the entire lenticule. With this preferred procedure, there are no vertical "steps" in the dissection. The deviations between the laser focus locations and the intended spherical surface dissections are also minimized.

Figure 8:
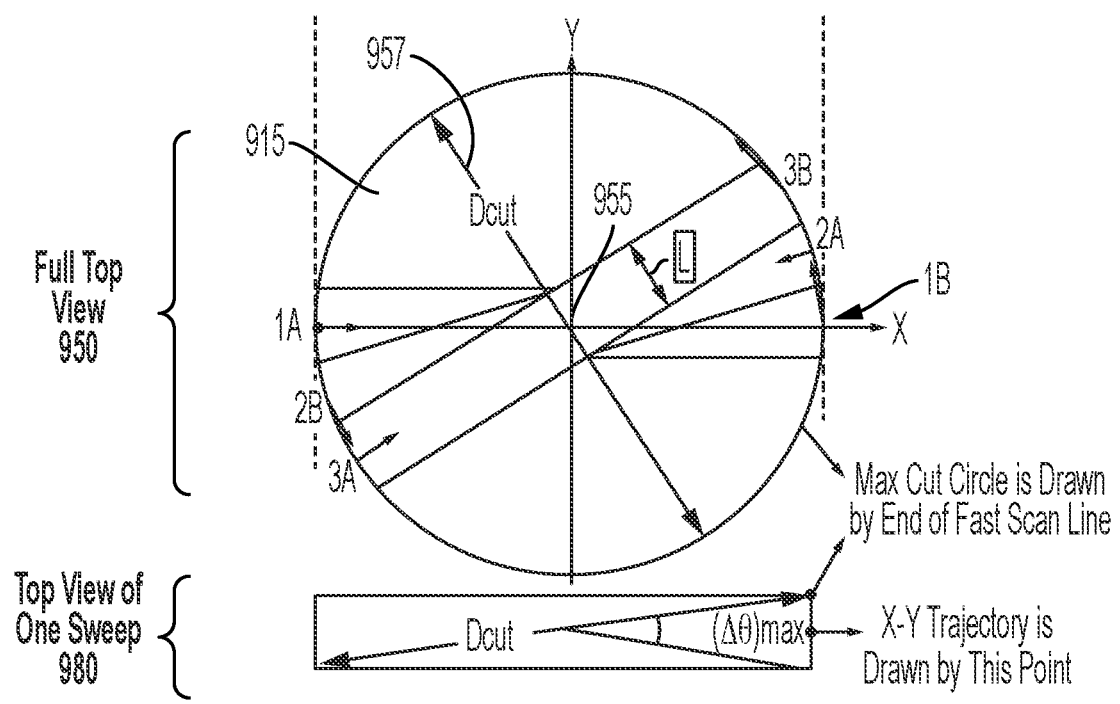

FIG. 8 shows a top view 950 of a lenticular incision 915 which illustrates three exemplary sweeps (1A to 1B), (2A to 2B) and (3A to 3B), with each sweep going through (i.e., going over) the lenticular incision apex 955. The incision has a diameter 957 ($D_{cuT}$). A top view 980 shows the top view of one exemplary sweep.

Note there that the example in FIG. 7 is a lenticule surface curved upwards, but the explanation applies equally to a lenticule surface curved downwards such as the bottom lenticule surfaces 102 and 303.

The "fast-scan-slow-sweep" scanning scheme may also be used to form the other incisions of the corneal lenticules in the above described embodiments. To form a flat bed incision 103 or 304, the fast scan line is kept at the same XY orientation and scanned by the XY and Z scanners in a raster scan pattern, i.e., forming sweeps along parallel lines or a serpentine path. To form a ring cut 302, the fast scan line is placed tangential to the ring and scanned in the Z direction, with scan line rotation between scans. To form the entry cut 101 or 301, the laser scan line is placed at the desired location and direction of the entry cut and scanned in the Z direction with or without rotation between scans.

In the corneal lenticule incision methods described above with reference to FIGS. 2 and 4, the controller 13 or 13B controls the laser source and scanners of the laser system to scan the focal spot of the laser beam in the eye tissue to form the various incisions according to the treatment plan. The depth measurement steps (e.g., step S210, S215) may be implemented using the auto-Z module 10. The user interface device used in steps S205 and S409 may be implemented by the communication device 15 or 15B.

It will be apparent to those skilled in the art that various modification and variations can be made in the corneal lenticule incision method and related apparatus of the present invention without departing from the spirit or scope of the invention. Thus, it is intended that the present invention cover modifications and variations that come within the scope of the appended claims and their equivalents.

What is claimed is:

1. A corneal lenticule formation method implemented in an ophthalmic laser system for forming a lenticule in a cornea of a patient's eye, comprising:
    (a) generating a laser beam;
    (b) scanning a laser beam focal spot in the cornea by executing a treatment plan, the treatment plan including a bottom segment defining a bottom lenticule incision and a top segment defining a top bed incision, wherein the bottom lenticule incision includes an optical zone having a shape determined by a defined optical power of the lenticule, the top bed incision has a flat shape, and the top bed incision is located above the bottom lenticule incision; and
    either: (c) in response to an interruption while executing the bottom segment of the treatment plan after the bottom lenticule incision is partially formed, revising the treatment plan to define a new bottom lenticule incision which has an identical shape as the bottom lenticule incision and is located below the partially formed bottom lenticule incision without coinciding with or intersecting the partially formed bottom lenticule incision, and scanning the laser beam focal spot by executing the revised treatment plan to form the new bottom lenticule incision;
    or: (d) in response to an interruption while executing the top segment of the treatment plan after the top bed incision is partially formed, revising the treatment plan to define a new top bed incision which has an identical shape as the top bed incision and is located above the partially formed top bed incision without coinciding with or intersecting the partially formed top bed incision, and scanning the laser beam focal spot by executing the revised treatment plan to form the new top bed incision.

2. The corneal lenticule formation method of claim 1, wherein step (c) further includes, before revising the treatment plan, measuring a depth of an apex of the partially formed bottom lenticule incision.

3. The corneal lenticule formation method of claim 2, wherein an apex of the new bottom lenticule incision is located 5-20 microns below the apex of the partially formed bottom lenticule incision.

4. The corneal lenticule formation method of claim 1, wherein step (d) further includes, before revising the treatment plan, measuring a depth of the partially formed top bed incision.

5. The corneal lenticule formation method of claim 4, wherein the new top bed incision is located 5-10 microns above the partially formed top bed incision.

6. The corneal lenticule formation method of claim 1, wherein in the treatment plan, the bottom segment is executed before the top segment.

7. The corneal lenticule formation method of claim 1, wherein in the treatment plan, the top segment is executed before the bottom segment.

8. The corneal lenticule formation method of claim 1, wherein the treatment plan further includes an entry segment which defines an entry cut, the entry cut extending upwardly from an outer edge of the bottom lenticule incision to reach an anterior surface of the cornea, the method further comprising:
    (e) in response to an interruption while executing the entry segment of the treatment plan after an entry cut is partially formed, revising the treatment plan to define a new entry cut which is aligned with the partially formed entry cut, and scanning the laser beam focal spot by executing the revised treatment plan.

9. The corneal lenticule formation method of claim 8, wherein in the treatment plan, the entry segment is executed before the bottom segment and the top segment.

10. The corneal lenticule formation method of claim 1, wherein the bottom lenticule incision and the top bed incision intersect each other near their respective peripheries to define an isolated lenticule volume.

11. The corneal lenticule formation method of claim 1, wherein the treatment plan further includes a ring segment which defines a ring cut, the ring cut having a ring shape and extending between the bottom lenticule incision and the top bed incision, wherein the bottom lenticule incision and the top bed incision both intersect the ring cut near their respective peripheries to define an isolated lenticule volume, the method further comprising:
    (e) in response to an interruption while executing the ring segment of the treatment plan after a ring cut is partially formed, revising the treatment plan to define a new ring cut which has a radius larger than a radius of the partially formed ring cut, the new ring cut being aligned concentrically with the partially formed ring cut, and scanning the laser beam focal spot by executing the revised treatment plan.

12. The corneal lenticule formation method of claim 11, wherein the radius of the new ring cut is larger than the radius of the partially formed ring cut by 20-100 microns.

13. The corneal lenticule formation method of claim 11, wherein step (b) includes:
    by a resonant scanner, scanning the laser beam to form a laser scan line, the scan line being a straight line having a predefined length and parallel to an XY plane; and
    by an XY scanner and a Z scanner, forming a plurality of sweeps of the scan line which collectively form the bottom lenticule incision, including, for each sweep: placing the scan line tangential to a parallel of latitude of the bottom lenticule incision and scanning the laser scan line along a meridian of longitude of the bottom lenticule incision, wherein the parallel of latitude is a circle on the bottom lenticule incision that is perpendicular to a Z axis and has a defined distance to an apex of the bottom lenticule incision, and the meridian of longitude is a curve that passes through the apex and has a defined angular position around the Z axis.

14. The corneal lenticule formation method of claim 11, wherein step (b) includes:
    by a resonant scanner, scanning the laser beam to form a laser scan line, the scan line being a straight line having a predefined length and parallel to an XY plane; and by an XY scanner, forming a plurality of parallel sweeps of the scan line which collectively form the top bed incision.

15. The corneal lenticule formation method of claim 1, wherein the treatment plan further includes an entry segment which defines an entry cut, the entry cut extending upwardly from an outer edge of the bottom lenticule incision to reach an anterior surface of the cornea, the method further comprising:

(e) in response to an interruption while executing the entry segment of the treatment plan after an entry cut is partially formed, revising the treatment plan to define a new entry cut that is located at a different angular position from the partially formed entry cut without coinciding with or intersecting the partially formed entry cut, and scanning the laser beam focal spot by executing the revised treatment plan.

16. A corneal lenticule formation method implemented in an ophthalmic laser system for forming a lenticule in a cornea of a patient's eye, comprising:

(a) generating a laser beam;
(b) scanning a laser beam focal spot in the cornea by executing a treatment plan, the treatment plan including, in a sequence, an entry segment defining an entry cut, a bottom segment defining a bottom lenticule incision, and a top segment defining a top bed incision, wherein the bottom lenticule incision includes an optical zone having a shape determined by a defined optical power of the lenticule, the top bed incision has a flat shape, the top bed incision is located above the bottom lenticule incision, the top bed incision and the bottom lenticule incision intersect each other near their respective peripheries to define an isolated lenticule volume, and the entry cut extends upwardly from an outer edge of the bottom lenticule incision; and either: (c) in response to an interruption while executing the entry segment of the treatment plan after the entry cut is partially formed, revising the treatment plan to define a new entry cut that is located at a different angular position from the partially formed entry cut without coinciding with or intersecting the partially formed entry cut, a new bottom lenticule incision, and a new top bed incision, and scanning the laser bean by executing the revised treatment plan to complete the entry cut and to form the new bottom lenticule incision and the new top bed incision;

or: (d) in response to an interruption while executing the bottom segment of the treatment plan after the entry cut is formed and the bottom lenticule incision is partially formed, revising the treatment plan to define a new bottom lenticule incision which has an identical shape as the bottom lenticule incision and is located below the partially formed bottom lenticule incision without coinciding with or intersecting the partially formed bottom lenticule incision, and a new top bed incision located above the new bottom lenticule incision, and scanning the laser beam focal spot by executing the revised treatment plan to form the new bottom lenticule incision and the new top bed incision;

or: (e) in response to an interruption while executing the top segment of the treatment plan after the entry cut and the bottom lenticule incision are formed and the top bed incision is partially formed, revising the treatment plan to define a new top bed incision which has an identical shape as the top bed incision and is located above the partially formed top bed incision without coinciding with or intersecting the partially formed top bed incision, and scanning the laser beam focal spot by executing the revised treatment plan to form the new top bed incision.

17. The corneal lenticule formation method of claim 16, wherein step (d) further includes, before revising the treatment plan, measuring a depth of an apex of the partially formed bottom lenticule incision, and wherein an apex of the new bottom lenticule incision is located 5-20 microns below the apex of the partially formed bottom lenticule incision.

18. The corneal lenticule formation method of claim 16, wherein step (e) further includes, before revising the treatment plan, measuring a depth of the partially formed top bed incision, and wherein the new top bed incision is located 5-10 microns above the partially formed top bed incision.

19. A corneal lenticule formation method implemented in an ophthalmic laser system for forming a lenticule in a cornea of a patient's eye, comprising:

(a) generating a laser beam;
(b) scanning a laser beam focal spot in the cornea by executing a treatment plan, the treatment plan including, in a sequence, an entry segment defining an entry cut, a ring segment defining a ring cut, a bottom segment defining a bottom lenticule incision, and a top segment defining a top bed incision, wherein the bottom lenticule incision includes an optical zone having a shape determined by a defined optical power of the lenticule, the top bed incision has a flat shape, the top bed incision is located above the bottom lenticule incision, the ring cut has a ring shape and extends between the top bed incision and the bottom lenticule incision, both the top bed incision and the bottom lenticule incision intersect the ring cut near their respective peripheries to define an isolated lenticule volume, and the entry cut extends upwardly from an outer edge of the bottom lenticule incision; and either: (c) in response to an interruption while executing the entry segment of the treatment plan after the entry cut is partially formed, revising the treatment plan to define a new entry cut that is located at a different angular position from the partially formed entry cut without coinciding with or intersecting the partially formed entry cut, a new ring cut, a new bottom lenticule incision, and a new top bed incision, and scanning the laser bean by executing the revised treatment plan to complete the entry cut and to form the new ring cut, the new bottom lenticule incision and the new top bed incision;

or: (d) in response to an interruption while executing the ring segment of the treatment plan after the entry cut is formed and the ring cut is partially formed, revising the treatment plan to define a new ring cut that has a radius larger than a radius of the partially formed ring cut and is aligned concentrically with the partially formed ring cut and without coinciding with or intersecting the partially formed ring cut, a new bottom lenticule incision, and a new top bed incision, and scanning the laser bean by executing the revised treatment plan to form the new ring, the new bottom lenticule incision and the new top bed incision;

or: (e) in response to an interruption while executing the bottom segment of the treatment plan after the entry cut and the ring cut are formed and the bottom lenticule incision is partially formed, revising the treatment plan to define a new bottom lenticule incision which has an identical shape as the bottom lenticule incision and is located below the partially formed bottom lenticule incision without coinciding with or intersecting the partially formed bottom lenticule incision, and a new top bed incision located above the new bottom lenticule incision, and scanning the laser beam focal spot by executing the revised treatment plan to form the new bottom lenticule incision and the new top bed incision; or: (f) in response to an interruption while executing the top segment of the treatment plan after the entry cut, the ring cut and the bottom lenticule incision are formed and the top bed incision is partially formed, revising the treatment plan to define a new top bed incision which has an identical shape as the top bed incision and is located above the partially formed top bed incision without coinciding with or intersecting the partially formed top bed incision, and scanning the laser beam focal spot by executing the revised treatment plan to form the new top bed incision.

20. The corneal lenticule formation method of claim 19, wherein the radius of the new ring cut is larger than the radius of the partially formed ring cut by 20-100 microns.

21. The corneal lenticule formation method of claim 19, wherein step (e) further includes, before revising the treatment plan, measuring a depth of an apex of the partially formed bottom lenticule incision, and wherein an apex of the new bottom lenticule incision is located 5-20 microns below the apex of the partially formed bottom lenticule incision; and wherein step (f) further includes, before revising the treatment plan, measuring a depth of the partially formed top bed incision, and wherein the new top bed incision is located 5-10 microns above the partially formed top bed incision.

* * * * *